(12) United States Patent
Thompson et al.

(10) Patent No.: US 7,109,201 B2
(45) Date of Patent: Sep. 19, 2006

(54) PIPERAZINE DERIVATIVES, THEIR PREPARATION AND USES IN THERAPY

(75) Inventors: Mervyn Thompson, Harlow (GB); Paul Adrian Wyman, Harlow (GB)

(73) Assignee: SmithKline Beecham plc, Middlesex (GB)

( * ) Notice: Subject to any disclaimer, the term of this patent is extended or adjusted under 35 U.S.C. 154(b) by 0 days.

(21) Appl. No.: 10/471,433

(22) PCT Filed: Mar. 11, 2002

(86) PCT No.: PCT/EP02/02632

§ 371 (c)(1), (2), (4) Date: Mar. 9, 2004

(87) PCT Pub. No.: WO02/074764

PCT Pub. Date: Sep. 26, 2002

(65) Prior Publication Data

US 2004/0142925 A1    Jul. 22, 2004

(30) Foreign Application Priority Data

Mar. 11, 2002 (EP) .................. 0106419

(51) Int. Cl.
 A61K 31/496   (2006.01)
 C07D 403/04   (2006.01)
 C07D 401/14   (2006.01)

(52) U.S. Cl. .................. 514/253.09; 514/254.09; 544/364; 544/373

(58) Field of Classification Search .............. 544/364, 544/373; 514/253.09, 254.09
See application file for complete search history.

(56) References Cited

FOREIGN PATENT DOCUMENTS

| WO | WO 95/06637 | 3/1995 |
| WO | WO 98/50358 | 11/1998 |
| WO | WO 99/29666 | 6/1999 |
| WO | WO 01/23374 | 4/2001 |

OTHER PUBLICATIONS

Gaster et al. Annual Reports in Medicinal Chemistry, vol. 33, p. 21-30 (1998).*

* cited by examiner

*Primary Examiner*—Emily Bernhardt
(74) *Attorney, Agent, or Firm*—James M. Kanagy; Stephen Venetianer; Charles M Kinzig

(57) ABSTRACT

Compounds of formula (I) or a pharmaceutically acceptable salt thereof are disclosed:

(I)

in which $R^a$ is a group of formula (i)

(i)

wherein $P^2$ is phenyl, naphthyl, heteroaryl or a 5 to 7 membered heterocyclic ring; $P^3$ is phenyl, naphthyl or heteroaryl; $R^1$ is $NR^4COR^5$, $NR^4SO_2R^5$, $CH_2NR^4SO_2R^5$, $CH_2NR^4COR^5$ or $CH_2NR^4CO_2R^5$ where $R^4$ and $R^5$ are independently hydrogen or $C_{1-6}$alkyl; $R^2$ and $R^3$ are independently halogen, $C_{1-6}$alkyl, $C_{3-6}$cycloalkyl, $C_{1-6}$alkoxy, $COC_{1-6}$alkyl, $haloC_{1-6}$alkyl, cyano or $NR^6R^7$ where $R^6$ and $R^7$ are independently hydrogen or $C_{1-6}$alkyl; b and c are independently 0, 1, 2 or 3; Y is a single bond, $CH_2$ or NH; W is —$(CR^9R^{10})_t$—where t is 2, 3 or 4 and $R^9$ and $R^{10}$ are independently hydrogen or $C_{1-6}$alkyl or W is a group CH=CH; $R^b$ is hydrogen, halogen, $C_{1-6}$alkyl, $haloC_{1-6}$alkyl, $COC_{1-6}$alkyl, cyano or $C_{1-6}$alkoxy; and $R^c$ is hydrogen or $C_{1-6}$alkyl. Processes for preparation of the compounds and their uses in therapy, particularly depression, are also disclosed.

9 Claims, No Drawings

PIPERAZINE DERIVATIVES, THEIR PREPARATION AND USES IN THERAPY

The present invention relates to novel piperazine derivatives, processes for their preparation, pharmaceutical compositions containing the same and to their use in the treatment of CNS and other disorders.

WO 95/06637 discloses a series of piperazine derivatives which are said to possess $5\text{-}HT_{1D}$ receptor antagonist activity. These compounds are alleged to be of use in the treatment of various CNS disorders such as depression. The human $5\text{-}HT_{1D}$ receptor is now known to be encoded by two distinct genes initially designated $5\text{-}HT_{1D\alpha}$ and $5\text{-}HT_{1D\beta}$ and subsequently redesignated as $5\text{-}HT_{1D}$ and $5\text{-}HT_{1B}$ respectively (P. R. Hartig et al, Trends in Pharmacological Science, 1996, 17, 103–105). WO 98/50538 and WO 98/47885 disclose a series of piperazine derivatives that are said to exhibit combined $5\text{-}HT_{1A}$, $5\text{-}HT_{1B}$ and $5\text{-}HT_{1D}$ receptor antagonist activity. WO 98/27058 discloses a series of carboxamide derivatives that are claimed to be $5\text{-}HT_6$ receptor antagonists.

A structurally novel class of compounds has now been found which exhibit $5\text{-}HT_{1B}$ receptor activity. In a first aspect, the present invention provides a compound of formula (I) or a pharmaceutically acceptable salt thereof:

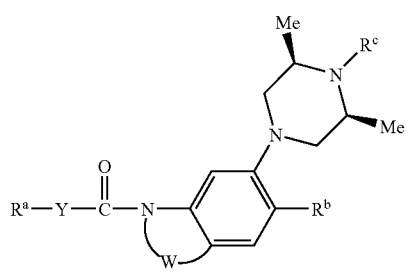

(I)

in which $R^a$ is a group of formula (i)

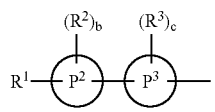

(i)

wherein $P^2$ is phenyl, naphthyl, heteroaryl or a 5 to 7 membered heterocyclic ring;

$P^3$ is phenyl, naphthyl or heteroaryl;

$R^1$ is $NR^4COR^5$, $NR^4SO_2R^5$, $CH_2NR^4SO_2R^5$, $CH_2NR^4COR^5$ where $R^4$ and $R^5$ are independently hydrogen or $C_{1-6}$alkyl;

$R^2$ and $R^3$ are independently halogen, $C_{1-6}$alkyl, $C_{3-6}$cycloalkyl, $C_{1-6}$alkoxy, $COC_{1-6}$alkyl, haloC$_{1-6}$alkyl, cyano or $NR^6R^7$ where $R^6$ and $R^7$ independently hydrogen or $C_{1-6}$alkyl;

b and c are independently 0, 1, 2 or 3;

Y is a single bond, $CH_2$ or NH;

W is $-(CR^9R^{10})_t-$ where t is 2, 3 or 4 and $R^9$ and $R^{10}$ are independently hydrogen or $C_{1-6}$alkyl or W is a group $CH=CH$;

$R^b$ is hydrogen, halogen, $C_{1-6}$alkyl, haloC$_{1-6}$alkyl, COC$_{1-6}$alkyl, cyano or $C_{1-6}$alkoxy;

$R^c$ is hydrogen or $C_{1-6}$alkyl.

Alkyl groups, whether alone or as part of another group, may be straight chain or branched.

The term "$C_{1-6}$alkyl" refers to an alkyl group having from one to six carbon atoms, in any isomeric form, such as methyl, ethyl, propyl, isopropyl, butyl, isobutyl, sec-butyl, tert-butyl, pentyl, neopentyl, sec-pentyl, n-pentyl, isopentyl, tert-pentyl and hexyl.

The term 'halogen' is used herein to describe, unless otherwise stated, fluorine, chlorine, bromine or iodine.

Where used herein the term naphthyl is intended, unless otherwise stated, to denote both naphth-1-yl and naphth-2-yl groups.

The term "heteroaryl" is intended to describe an aromatic or a benzofused aromatic ring containing 1 to 3 heteroatoms selected from oxygen, nitrogen and sulphur. Suitable examples of such aromatic rings include thienyl, furyl, pyrrolyl, triazolyl, imidazolyl, oxazolyl, thiazolyl, oxadiazolyl, isothiazolyl, isoxazolyl, thiadiazolyl, pyrazolyl, pyrimidyl, pyridazinyl, pyrazinyl and pyridyl. Suitable examples of such benzofused aromatic rings include quinolinyl, isoquinolinyl, indolyl, benzofuryl, benzothienyl, benzimidazolyl, benzoxazolyl and the like.

The term "$C_{3-6}$cycloalkyl" refers to a cycloalkyl group consisting of from 3 to 6 carbon atoms, such as cyclopropane, cyclobutane, cyclopentane or cyclohexane.

The term "$C_{1-6}$alkoxy" refers to a straight chain or branched chain alkoxy (or "alkyloxy") group consisting of from one to six carbon atoms, such as methoxy, ethoxy, propoxy, isopropoxy, butoxy, isobutoxy, sec-butoxy, tert-butoxy, pentoxy, neopentoxy, sec-pentoxy, n-pentoxy, isopentoxy, tert-pentoxy and hexoxy.

The term "haloC1–6alkyl" refers to a $C_{1-6}$alkyl group which is substituted by one or more halogens. Examples include $CF_3$.

The term "5–7 membered heterocyclic ring" is used herein to mean a non aromatic ring containing 1 to 3 heteroatoms selected from oxygen, nitrogen and sulphur. Suitable examples of such heterocyclic rings include piperidinyl, piperazinyl, pyrrolidinyl, imidazolidinyl, pyrazolidinyl, oxazolinyl, isothiazolidinyl, thiazolidinyl, dioxolanyl, thiazinanyl, dioxanyl and morpholinyl.

The heteroaryl and 5–7 membered heterocyclic rings, as described above, may be linked to the remainder of the molecule via a carbon atom or, when present, a suitable nitrogen atom.

Within the definition of $R^a$ formula (I)

When $P^3$ is heteroaryl a particularly preferred group is pyridyl. $P^3$ is preferably phenyl or pyridyl.

$P^2$ is preferably phenyl or a heteroaryl group such as pyridyl, pyrimidinyl, pyrazinyl, oxadiazolyl or oxazolyl. $P^2$ is preferably phenyl or pyridyl.

When b is other than 0, preferred $R^2$ include halogen (particularly fluoro and chloro), or $C_{1-6}$alkyl group (particularly methyl). When b is 2 or 3 the groups $R^2$ may be the same or different. Preferably b is 0 or 1.

When c is other than 0, preferred $R^3$ groups are halogen (particularly fluoro and chloro) and $C_{1-6}$alkyl group (particularly methyl). When c is 2 or 3 the groups $R^3$ may be the same or different. Preferably c is 0 or 1.

Y is preferably a single bond.

It will be appreciated that when W is a group —CH=CH— an indole ring is formed. Within the definition of the group W, the groups $R^9$ and $R^{10}$ are each preferably hydrogen and t is preferably 2 or 3, most preferably 2.

$R^b$ is preferably hydrogen, halogen (particularly chloro or fluoro), $C_{1-6}$alkoxy group (particularly methoxy) or $C_{1-6}$alkyl group (particularly methyl).

$R^c$ is preferably hydrogen or methyl.

Preferred compounds of this invention are examples E1–E27 (as described below) or a pharmaceutically acceptable salt thereof.

The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1–19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Certain of the compounds of formula (I) may form acid addition salts with one or more equivalents of the acid. The present invention includes within its scope all possible stoichiometric and non-stoichiometric forms.

The compounds of formula (I) may be prepared in crystalline or non-crystalline form, and, if crystalline, may optionally be hydrated or solvated. This invention includes within its scope stoichiometric hydrates as well as compounds containing variable amounts of water and/or solvent.

Certain compounds of formula (I) are capable of existing in stereoisomeric forms (e.g. geometric (or "cis-trans") isomers, diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

Compounds of the invention can be prepared using procedures known in the art. In a further aspect the present invention also provides a process for the preparation of a compound of formula (I) or a pharmaceutically acceptable salt thereof which comprises either:

(a) where Y is NH, coupling a compound of formula (II):

$$R^a-NH-C=O \quad (II)$$

in which $R^a$ is as defined in formula (I), with a compound of formula (III):

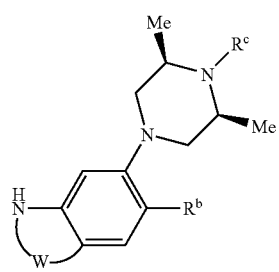

(III)

in which W, $R^b$ and $R^c$ are as defined in formula (I); or (b) where Y is a single bond or $CH_2$, reacting a compound of formula (IV):

(IV)

in which $R^a$ is as defined in formula (I) and L is an appropriate leaving group, with a compound of formula (III) as defined above; or (c) where Y is a single bond or $CH_2$, reacting a compound of formula (V):

(V)

in which $R^a$ is as defined in formula (I) and R' is a $C_{1-6}$alkoxyl group, with a compound of formula (III) as defined above;

and optionally thereafter for either process (a), (b) or (c):
   removing any protecting groups, and/or
   converting a compound of formula (I) into another compound of formula (I), and/or
   forming a pharmaceutically acceptable salt.

The reaction in process (a) is conveniently effected in an organic solvent such as dichloromethane.

In process (b) the leaving group L may be a halogen e.g. chloro group and the reaction may be carried out in an inert organic solvent such as tetrahydrofuran or dichloromethane at ambient or elevated temperature in the presence of a base such as triethylamine or pyridine. Alternatively L may be an O-benzotriazole group, prepared from hydroxybenzotriazole and a carbodiimide, and the reaction may be carried out in an inert organic solvent such as tetrahydrofuran, dichloromethane or dimethylformamide at ambient or elevated temperature.

The reaction in process (c) is typically carried out in a solvent such as toluene at elevated temperature in the presence of trimethylaluminium.

Compounds of formula (I) can be converted into further compounds of formula (I) using standard techniques. The following examples are given by way of illustration of this point rather than limitation. For compounds of formula (I) wherein $R^c$ is hydrogen, it is possible to introduce a $C_{1-6}$alkyl group by conventional alkylation using 1 molar equivalent of a $C_{1-6}$alkyl halide and 1 molar equivalent of a suitable base in an inert solvent. For compounds of formula (I) wherein W is a group $-CH_2CH_2-$, it is possible to convert this to a group wherein W is $-CH=CH-$ with an oxidising agent such as 2,3-dichloro-5,6dicyano-1,4-benzoquinone in an inert solvent such as dichloromethane or toluene.

Intermediate compounds of formula (II), (III) and (IV) are either commercially available or can be prepared using methods described herein, by methods known to those skilled in the art or by analogous methods thereto. For example, where intermediates of formula (IV) are derived from phenylacetic acids, the latter may be prepared from the corresponding benzoic acids by standard homologation methods involving reduction to the benzyl alcohol, followed by conversion to the benzyl bromide, displacement with an inorganic cyanide to afford the benzonitrile, followed by acid or base hydrolysis.

It will be appreciated to those skilled in the art that it may be necessary to protect certain reactive substituents during some of the above procedures. Standard protection and deprotection techniques can be used, such as those described in Greene T. W. Protective groups in organic synthesis, New York, Wiley (1981). For example, primary amines can be protected as phthalimide, benzyl, benzyloxycarbonyl or trityl derivatives. Carboxylic acid groups can be protected as esters. Aldehyde or ketone groups can be protected as acetals, ketals, thioacetals or thioketals. Deprotection of such groups is achieved using conventional procedures well known in the art. For example, protecting groups such as t-butyloxycarbonyl may be removed using an acid such as hydrochloric or trifluroroacetic acid in a suitable solvent such as dichloromethane, diethylether, isopropanol or mixtures thereof.

Pharmaceutically acceptable salts may be prepared conventionally by reaction with the appropriate acid or acid derivative.

The involvement of serotonin (5-hydroxytryptamine; 5-HT) receptors in a number of pharmacological effects has been reviewed by R. A. Glennon in "Serotonin Receptors: Clinical Implications", Neuroscience and Behavioural Reviews, 1990, 14, 35 and by L. O. Wilkinson and C. T. Dourish in "Serotonin Receptor Subtypes: Basic and Clinical Aspects" S. Peroutka Ed., John Wiley and Sons, New York, 1991 p.147.

Serotonin receptors have been implicated in pharmacological effects such as mood disorders including depression (both bipolar and unipolar), single or recurrent major depressive episodes with or without psychotic features, catatonic features, melancholic features, atypical features or postpartum onset, depression resulting from a general medical condition including, but not limited to, myocardial infarction, diabetes, miscarriage or abortion, etc., seasonal affective disorder and dysthymia, anxiety disorders, including generalised anxiety and social anxiety disorder, panic disorder, agoraphobia, social phobia, obsessive compulsive disorder and post-traumatic stress disorder, memory disorders, including dementia, amnesic disorders and age-associated memory impairment; disorders of eating behaviours, including anorexia nervosa and bulimia nervosa, sleep disorders (including narcolepsy, dyssomnia, insomnia, sleep apnea and disturbances of circadian rhythm), motor disorders such as Parkinson's disease, dementia in Parkinson's disease, neuroleptic-induced Parkinsonism and tardive dyskinesias, pain disorders (particularly neuropathic pain), as well as other psychiatric disorders such as schizophrenia and psychosis. Serotonin receptor ligands have been shown to be of use in the treatment of emesis and nausea and may also be of use in endocrine disorders such as hyperlactinaemia, vasospasm (particularly in the cerebral vasculature), cerebellar ataxia and hypertension, as well as disorders of the gastrointestinal tract where changes in motility and secretion are involved such as irritable bowel syndrome, and in treatment of withdrawal symptoms from abuse of drugs such as of cocaine, ethanol, nicotine, benzodiazepines, alcohol, caffeine, phencyclidine (phencyclidine-like compounds), opiates (e.g. cannabis, heroin, morphine), sedative ipnotic, amphetamine or amphetamine-related drugs (e.g. dextroamphetamine, methylamphetamine) or a combination thereof. They may also be of use in the treatment of pre-menstrual tension, sexual dysfunction and hypothermia.

Ligands with high affinity for the $5\text{-}HT_1$ receptors are well recognised as having therapeutic utility for the treatment of the above conditions. It has been suggested that a selective $5\text{-}HT_{1B}$ receptor antagonist should act as a fast onset anti-depressant (P. Blier Trends Pharmacol. Sci. 1994, 15, 220).

Accordingly, the present invention provides a compound of formula (I) or a pharmaceutically acceptable salt for use in therapy.

In particular, the present invention provides for a compound of formula (I) or a pharmaceutically acceptable salt for use in the treatment of depression (which includes bipolar depression, unipolar depression, single or recurrent major depressive episodes with or without psychotic features, catatonic features, melancholic features, atypical features or postpartum onset, depression resulting from a general medical condition including, but not limited to, myocardial infarction, diabetes, miscarriage or abortion, etc., seasonal affective disorder and dysthymia), anxiety disorders including generalised anxiety and social anxiety disorder, panic disorders, schizophrenia, psychosis, agoraphobia, social phobia, obsessive compulsive disorder and post-traumatic stress disorder, memory disorders, including dementia, amnesic disorders and age-associated memory impairment, disorders of eating behaviours, including anorexia nervosa and bulimia nervosa, sleep disorders (including narcolepsy, dyssomnia, insomnia, sleep apnea and disturbances of circadian rhythm), motor disorders such as Parkinson's disease, dementia in Parkinson's disease, neuroleptic-induced Parkinsonism and tardive dyskinesias, pain disorders (particularly neuropathic pain), emesis and nausea, endocrine disorders such as hyperlactinaemia, vasospasm (particularly in the cerebral vasculature), cerebellar ataxia, hypertension, gastrointestinal disorders where changes in motility and secretion are involved, such as irritable bowel syndrome, treatment of withdrawal symptoms from abuse of drugs such as of cocaine, ethanol, nicotine, benzodiazepines, alcohol, caffeine, phencyclidine (phencyclidine-like compounds), opiates (e.g. cannabis, heroin, morphine), sedative ipnotic, amphetamine or amphetamine-related drugs (e.g. dextroamphetamine, methylamphetamine) or a combination thereof, pre-menstrual tension, sexual dysfunction and hypothermia. In particular, the present invention provides for a compound of formula (I) or a pharmaceutically acceptable salt for use in the treatment of depression.

It is to be understood that the term "treatment" as used herein includes prophylaxis as well as alleviation of established symptoms.

In a further aspect the invention provides a method of treating a disorder where an antagonist of the $5\text{-}HT_{1B}$ receptor is beneficial, particularly the aforementioned disorders, more particularly depression, which comprises administering a safe and therapeutically effective amount of compound of formula (I) or a pharmaceutically acceptable salt to a patient in need thereof.

In another aspect, the invention provides the use of a compound of formula (I) or a pharmaceutically acceptable salt thereof In the manufacture of a medicament for the treatment of disorders in which an antagonist of the $5\text{-}HT_{1B}$ receptor is beneficial, particularly the aforementioned disorders, more particularly depression.

The affinities of the compounds of this invention for the $5\text{-}HT_{1B}$ receptor can be determined by the following radio-ligand binding assay. CHO cells expressing $5\text{-}HT_{1B}$ receptors ($4 \times 10^7$ cells/ml) are homogenised in Tris buffer $Mg^{2+}$ and stored in 1.0 ml aliquots. 0.4 ml of a cell suspension is incubated with [$^3$H]-5-HT (4 nM) in Tris Mg HCl buffer (pH 7.7) and test drug, at 37° C. for 45 minutes. Each test drug is tested at 10 concentrations (0.01 mM to 0.3 nM final concentration), with non-specific binding defined using 0.01 mM 5-HT. The total assay volume is 0.5 ml. Incubation is stopped by rapid filtration using a Tomtec Harvester (filters pre-washed in 0.3% polyethylenimine) and radioactivity measured by Topcount scintillation counting. pKi values are calculated from the $IC_{50}$ generated by an iterative least squares curve fitting programme.

All examples tested in accordance with this radioligand binding assay were found to have a pKi>7.0 at $5\text{-}HT_{1B}$ receptors with many demonstrating a pKi in the higher range of 8.0–8.5.

The selectivity of the compounds of this invention for $5\text{-}HT_{1B}$ receptors can be determined using binding assay methods which are well known to those skilled in the art. All examples tested were found to have a greater than a 10-fold selectivity over $5\text{-}HT_{1D}$ receptors and a greater than 50-fold selectivity over other binding sites within the CNS, in particular, other 5-HT receptor sub-types and dopaminergic receptors. Many examples were found to have a greater than a 30-fold selectivity over $5\text{-}HT_{1D}$ receptors and a greater than 80-fold selectivity over other binding sites.

The intrinsic activity of the compounds of this invention can be determined according to the following procedure. CHO cell membranes stably expressing human $5\text{-}HT_{1B}$ receptors are homogenised in HEPES/EDTA buffer and stored in 1 ml aliquots, and $[^{35}S]GTP\gamma S$ binding studies are carried out essentially as described by Lazareno et at, (Life Sci., 1993, 52, 449) with some minor modifications. Membranes from $10^6$ cells are pre-incubated at 30° C. for 30 minutes in 20 mM HEPES buffer (pH 7.4) in the presence of $MgCl_2$ (3 mM), NaCl (100 mM), GDP (10 μM) and ascorbate (0.2 mM), with or without compounds. The reaction is started by the addition of 50 μl of $[^{35}S]GTP\gamma S$ (100 pm, assay concentration) followed by a further 30 minutes incubation at 30° C. Non-specific binding was determined using non-radiolabelled GTPγS (20 μM) added prior to the membranes. The reaction is terminated by rapid filtration through Whatman GF/B grade filters followed by 5×1 ml washes with ice cold HEPES (20 mM)/$MgCl_2$ (3 mM) buffer. Radioactivity is measured using liquid scintillation spectrometry. This procedure is hereafter referred to as the $[^{35}S]GTP\gamma S$ functional assay.

It has been found, using the $[^{35}S]GTP\gamma S$ functional assay, that certain compounds of formula (I) show varying levels of intrinsic efficacy, which is defined by a scale in which the value 1.0 defines the maximum response elicited by the agonist 5-HT, 0.0 defines antagonism and a negative value indicates inverse agonism. The difficulties in describing intrinsic activity of drugs acting at G protein coupled receptors is recognised in the art (Hoyer and Boddeke, Trends in Pharmacological Sciences, July 1993, [Vol. 14], page 270–275). We believe that however these ligands are classified according to this functional assay, the compounds of this invention will be useful antidepressants in vivo. It is believed that the preferred compounds of this invention will display $5\text{-}HT_{1B}$ antagonist activity in vivo and that such compounds will have a rapid onset of action. A rapid onset of action is particularly advantageous for antidepressant compounds: by 'rapid onset of action' we mean that a therapeutic response is seen within 7 days from first administration of the compound, as opposed to a period of about 21 days or more which is typical of SSRI's, tricyclic antidepressants and buspirone.

Compounds of formula (I) which have an intrinsic activity of 0.5 or less in the in vitro $[^{35}S]GTP\gamma S$ functional assay are preferred, as these compounds are more likely to be full antagonists in vivo. Particularly preferred compounds of this invention have an intrinsic activity in the range 0.0–0.3 or are inverse agonists in this functional assay.

It has been found that the compounds of this invention have a particularly advantageous profile in that they demonstrate high affinity and selectivity for the $5\text{-}HT_{1B}$ receptor together with low intrinsic activity in the $[^{35}S]GTP\gamma S$ functional assay.

It will be appreciated by those skilled in the art that the compounds according to the invention may advantageously be used in conjunction with one or more other therapeutic agents, for instance, different antidepressant agents, such as 5HT3 antagonists, serotonin agonists, NK-1 antagonists, selective serotonin reuptake inhibitors (SSRI), noradrenaline re-uptake inhibitors (SNRI), tricyclic antidepressants and/or dopaminergic antidepressants.

Suitable 5HT3 antagonists which may be used in combination of the compounds of the inventions include for example ondansetron, granisetron, metoclopramide.

Suitable serotonin agonists which may be used in combination with the compounds of the invention include sumatriptan, rauwolscine, yohimbine, metoclopramide.

Suitable SSRIs which may be used in combination with the compounds of the invention include fluoxetine, citalopram, femoxetine, fluvoxamine, paroxetine, indalpine, sertraline, zimeldine.

Suitable SNRIs which may be used in combination with the compounds of the invention include venlafaxine and reboxetine.

Suitable tricyclic antidepressants which may be used in combination with a compound of the invention include imipramine, amitriptiline, chlomipramine and nortriptiline.

Suitable dopaminergic antidepressants which may be used in combination with a compound of the invention include bupropion and aminéptine.

It will be appreciated that the compounds of the combination or composition may be administered simultaneously (either in the same or different pharmaceutical formulations), separately or sequentially.

In order to use the compounds of formula (I) in therapy, they will normally be formulated into a pharmaceutical composition in accordance with standard pharmaceutical practice. The present invention also provides a pharmaceutical composition, which comprises a compound of formula (I) or a pharmaceutically acceptable salt thereof, and a pharmaceutically acceptable carrier or excipient.

In a further aspect, the present invention provides a process for preparing a pharmaceutical composition, the process comprising mixing a compound of formula (I) or a pharmaceutically acceptable salt thereof and a pharmaceutically acceptable carrier or excipient.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents (e.g. pregelatinised maize starch, polyvinylpyrrolidone or hydroxypropyl methylcellulose), fillers (e.g. lactose, microcrystalline cellulose or calcium hydrogen phosphate), tabletting lubricants (e.g. magnesium stearate, talc or silica), disintegrants (e.g. potato starch or sodium starch glycollate) and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents(e.g. sorbitol syrup, cellulose derivatives or hydrogenated edible fats), emulsifying agents(e.g. lecithin or acacia), non-aqueous vehicles (which may include edible oils eg. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound.

For parenteral administration, fluid unit dosage forms are prepared utilising a compound of the invention or pharmaceutically acceptable salt thereof and a sterile vehicle. Formulations for injection may be presented in unit dosage form e.g. in ampoules or in multi-dose, utilising a compound of the invention or pharmaceutically acceptable salt thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device. Thus compounds of formula (I) may be formulated for oral, buccal, parenteral, topical (including ophthalmic and nasal), depot or rectal administration or in a form suitable for administration by inhalation or insufflation (either through the mouth or nose).

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three times a day. Such therapy may extend for a number of weeks or months.

All publications, including but not limited to patents and patent applications, cited in this specification are herein incorporated by reference as if each individual publication were specifically and individually indicated to be incorporated by reference herein as though fully set forth.

The following descriptions and Examples illustrate the preparation of compounds of the invention.

Description 1

1-Acetyl-6-bromo-5-methoxyindoline (D1)

A stirred solution of 1-acetyl-6-bromoindolin-5-ol (Tetrahedron 1973, 29(8), 1115; 40 g, 0.15 mole) in DMF (500 ml) was treated with $K_2CO_3$ (61 g, 0.45 mole) and iodomethane (11.7 ml, 0.19 mole) and maintained at room temperature for 20 h, then concentrated under vacuum to 200 ml. The residue was treated with water (200 ml) and the precipitate filtered off, dried and recrystallised from EtOAc to afford the title compound as a white solid (35.7 g, 85%). $MH^+$ 270/272.

Description 2 cis-1-Acetyl-6-(3,5-dimethylpiperazin-1-yl)-5-methoxyindoline (D2)

A mixture of palladium (II) acetate (830 mg, 3.7 mmole), 2,2'-bis(diphenylphosphino)-1,1'-binaphthyl (3.46 g, 5.5 mmole) and cesium carbonate (18.1 g, 56 mmole) in dry degassed 1,4-dioxane (200 ml) under argon was sonicated at 28° C. for 0.5 h producing a pink heterogeneous mixture. This was treated with D1 (10 g, 37 mmole) followed by cis-2,6-dimethylpiperazine (12.6 g, 110 mmole) and heated with rapid stirring at reflux for 96 h. The mixture was allowed to cool, filtered through Kieselguhr and then concentrated under vacuum. The residue was treated with EtOAc and 2M HCl acid, shaken well and the aqueous layer separated, basified by addition of $K_2CO_3$ and extracted with DCM. The extract was dried (Na$_2$SO$_4$) and concentrated under vacuum to afford the title compound as a pale orange solid (7.1 g, 63%). MH$^+$ 304.

Description 3 cis-6-(3,5-Dimethylpiperazin-1-yl)-5-methoxyindoline (D3)

A stirred solution of D2 (1.6 g, 5 mmole) in 2M HCl acid (50 ml) was heated under reflux for 2 h, then allowed to cool, basified with K$_2$CO$_3$ and extracted with DCM. The extract was dried (Na$_2$SO$_4$) and concentrated under vacuum to afford the title compound as a pale orange solid (1.4 g, 100%). MH$^+$ 276.

Description 4

6-Bromo-5-fluoroindoline

A solution of 5-fluoroindoline (4.65 g, 34 mmole) in conc. H$_2$SO$_4$ acid (60 ml) under argon was treated with silver sulfate (5.5 g, 18 mmole) and stirred for 0.5 h, then cooled to −5° C. and treated dropwise over 15 min with bromine (5.6 g, 35 mmole). The mixture was maintained at −5° C. for 0.5 h, then allowed to warm to room temperature over 1 h, before adding cautiously to well stirred ice/water (600 ml). The mixture was filtered through Kieselguhr, then basified by addition of 40% NaOH solution and extracted with Et$_2$O (2×300 ml). The combined extract was dried (Na$_2$SO$_4$) and concentrated under vacuum to afford the title compound as a beige solid (6.5 g, 89%). MH$^+$ 216/218.

Description 5

1-Acetyl-6-bromo-5-fluoroindoline

A stirred solution of D4 (6.5 g, 30 mmole) in DCM (60 ml) was treated with AC$_2$O (3.8 ml, 40 mmole) and stirred at room temperature for 1 h, then concentrated under vacuum. The residue was chromatographed on neutral alumina eluting with Et$_2$O to afford the title compound as a beige solid (7.2 g, 93%). MH$^+$ 258/260.

Description 6 cis-6-(3,5-Dimethylpiperazin-1-yl)-5-fluoroindoline (D6)

The title compound was prepared from D5 by reaction with cis-3,5-dimethylpiperazine using a similar procedure to Description 2 (82%) followed by hydrolysis as in Description 3 (96%). The product was isolated as a pale brown solid. MH$^+$ 250.

Description 7

Methyl 4-(6-acetamido-2-methylpyridin-3-yl)benzoate (D7)

A stirred solution of methyl 4-(6-amino-2-methylpyridin-3-yl)benzoate (Description 7 in EP 97/17351, 300 mg, 1.2 mmole) and pyridine (0.16 ml, 2.0 mmole) in DCM (35 ml) at 0° C. under argon was treated with acetyl chloride (120 mg, 1.5 mmole) and allowed to warm to room temperature over 1 h. Additional acetyl chloride (120 mg) was added, the mixture maintained at room temperature for a further 1 h, then washed with 10% Na$_2$CO$_3$ solution, dried (Na$_2$SO$_4$) and concentrated under vacuum to afford the title compound as a white solid (344 mg, 98%).

$^1$H NMR (250 MHz, CDCl$_3$) δ8.15–8.00 (m, 3H), 7.93 (s, 1H), 7.56 (dd, 1H), 7.39 (d, 2H), 7.26 (d, 1H), 3.95 (s, 3H), 2.40 (s, 3H), 2.23 (s, 3H).

Description 8

Methyl 4-[6-(methanesulfonamido)-2-methylpyridin-3-yl]benzoate (D8)

A stirred solution of methyl 4-(6-amino-2-methylpyridin-3-yl)benzoate (Description 7 in EP 97/17351, 300 mg, 1.2 mmole) and pyridine (0.16 ml, 2.0 mmole) in DCM (35 ml) at 0° C. under argon was treated with methanesulfonyl chloride (215 mg, 1.5 mmole), then allowed to warm to room temperature and stir for 20 h. Additional methanesulfonyl chloride (215 mg, 1.5 mmole) and Et$_3$N (200 mg, 2 mmole) were added. After 1 h at room temperature the mixture was washed with 10% Na$_2$CO$_3$ solution, dried (Na$_2$SO$_4$) and concentrated under vacuum to leave the bis-sulfonamide as a beige solid. This was dissolved in THF (10 ml), treated with tetrabutylammonium fluoride (1.6 ml of 1M in THF, 1.6 mmole) and stirred at room temperature for 18 h. Additional tetrabutylammonium fluoride solution (1.0 ml) was added and the mixture heated at 40° C. for 1 h, then concentrated under vacuum. The residue was treated with 10% Na$_2$CO$_3$ solution and extracted with EtOAc. The extract was dried (Na$_2$SO$_4$), concentrated under vacuum and the residue chromatographed on silica gel eluting with 0–15% EtOAc/DCM to afford the title compound as a white solid (214 mg, 32%).

$^1$H NMR (250 MHz, CDCl$_3$) δ8.11 (d, 2H), 7.55 (d, 1H), 7.37 (d, 2H), 7.06 (d, 1H), 3.96 (s, 3H), 3.21 (s, 3H), 2.42 (s, 3H). NH not discernible.

Description 9

Methyl 4-[6-(N-acetyl-N-methyl)amino-2-methylpyridin-3-yl]benzoate (D9)

A solution of D7 (120 mg, 6.40 mmole) in dry DMF (3 ml) at room temperature under argon was treated with sodium hydride (18 mg of 60% oil dispersion, 0.45 mmole), stirred for 20 min, then treated with iodomethane (61 mg, 0.43 mmole). The mixture was maintained at room temperature for 1 h, then added to 10% Na$_2$CO$_3$ solution (50 ml) and extracted with EtOAc. The extract was washed with water, dried (Na$_2$SO$_4$) and concentrated under vacuum to afford the title compound as a beige solid (110 mg, 87%).

$^1$H NMR (250 MHz, CDCl$_3$) δ8.13 (d, 2H), 7.61 (d, 1H), 7.43 (d, 2H), 7.20 (br d, 1H), 3.96 (s, 3H), 3.42 (s, 3H), 2.49 (s, 3H), 2.16 (s, 3H).

Description 10

Methyl 4-[6-(N-methanesulfonyl-N-methylamino)-2-methylpyridin-3-yl]benzoate (D10)

The title compound was prepared from D8 using a similar procedure to Description 9 as a yellow gum (96%).

$^1$H NMR (250 MHz, CDCl$_3$) δ8.11 (d, 2H), 7.57 (d, 1H), 7.40 (d, 2H), 7.30 (d, 1H), 3.96 (s, 3H), 3.45 (s, 3H), 3.11 (s, 3H), 2.46 (s, 3H).

Description 11

Methyl 4'-acetamido-2'-methylbiphenyl-4-carboxylate (D11)

The title compound was prepared from methyl 4'-amino-2'-methylbiphenyl-4-carboxylate (Description 2 in WO 97/34901) following a similar procedure to Description 7. MH+ 269.

Description 12

Methyl 4'-(methanesulfonamido)-2'-methylbiphenyl-4-carboxylate (D12)

The title compound was prepared from methyl 4'-amino-2'-methylbiphenyl-4-carboxylate (Description 2 in WO 97/34901) following a similar procedure to Description 8. MH+ 305.

Description 13 cis-5-Chloro-6-(3,5-dimethylpiperazin-1-yl)indoline (D13)

The title compound can be prepared from 5-chloroindoline using similar procedures to those described in D4, D5 and D6 above. MH+ 266.

Description 14 cis-6-(3,5-Dimethylpiperazin-1-yl)-5-methylindoline (D14)

The title compound was prepared from 5-methylindoline using similar procedures to those described in D4, D5 and D6 above. MH+ 246.

Description 15 cis-1-Acetyl-5-methoxy-6-(3,4,5-trimethylpiperazin-1-yl)indoline (D15)

A stirred solution of D2 (1.48 g, 4.9 mmole) in MeOH (50 ml) at room temperature under Ar was treated with aqueous formaldehyde (2.4 ml of 37% w/v, 29 mmole), followed by portionwise addition of NaBH₃CN (920 mg, 15 mmole). The mixture was stirred at room temperature for 3 h, then concentrated under vacuum and the residue treated with 10% Na₂CO₃ solution and extracted with DCM. The extract was dried (Na₂SO₄) and concentrated under vacuum to afford the title compound as a yellow solid (1.4 g, 90%). MH+ 318.

Description 16

5-Methoxy-6-(3,4,5-trimethylpiperazin-1-yl)indole (D16)

The title compound was prepared from D16 using a similar procedure to Description 3. MH+ 276.

EXAMPLE 1

N-[5-(4-{[6-[(3R,5S)-3,5-dimethyl-1-piperazinyl]-5-(methoxy)-2,3-dihydro-1H-indol-1-yl]carbonyl}phenyl)-6-methyl-2-pyridinyl]acetamide (E1)

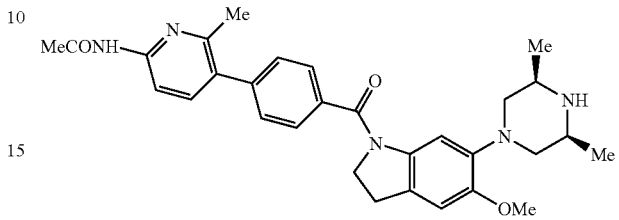

A stirred solution of D3 (40 mg, 150 umole) in toluene (2 ml) at room temperature under argon was treated with 2M trimethylaluminium in toluene (0.15 ml, 300 umole) and maintained for 15 min, then a solution of D7 (57 mg, 200 umole) in toluene (3 ml) was added and the mixture heated at 90° C. for 1 h. The solution was allowed to cool, then added directly to a silica gel column (5 g) and eluted initially with 2% MeOH/DCM to remove high Rf impurities, then with 10% MeOH/DCM to afford the product. This was triturated with Et₂O/DCM to afford the title compound as a beige solid (35 mg, 82%).

$^1$H NMR (250 MHz, CDCl₃) δ8.08 (d, 1H), 8.00 (br s, 1H), 7.94 (s, 1H), 7.64 (d, 2H), 7.58 (d, 1H), 7.40 (d, 2H), 6.75 (s, 1H), 3.80–4.00 (br m, 2H), 3.86 (s, 3H), 3.50–3.30 (br m, 2H), 3.25–2.85 (m, 5H), 2.43 (s, 3H), 2.35–2.15 (br m, 2H), 2.23 (s, 3H), 1.20–0.80 (br m, 6H). MH+ 514.

EXAMPLE 2

N-[4'-({6-[(3R,5S)-3,5-dimethyl-1-piperazinyl]-5-fluoro-1H-indol-1-yl}carbonyl)-2-methyl-4-biphenylyl]acetamide (E2)

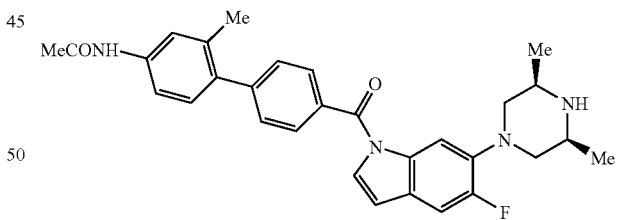

A solution of E9 (37 mg, 70 umole) in DCM (5 ml) was treated with DDQ (25 mg, 100 umole) and stirred at room temperature for 1 h, then treated with 10% Na₂CO₃ solution and the organic layer separated, filtered through a short column of Diatomaceous Earth and concentrated under vacuum to afford the title compound as a beige solid (12 mg, 33%). MH+ 499.

Examples E3–14 and E21–27 were prepared by a similar procedure to Example 1 from the appropriate indoline (D3, D6, D13 or D14) and methyl ester (D8, D9, D10, D11, D12 or Description 21 in WO 96/19477). Examples E15–20 were prepared by a similar procedure to Example 2 by oxidation of indoline E10, E6, E13, E14, E12 and E23 respectively.

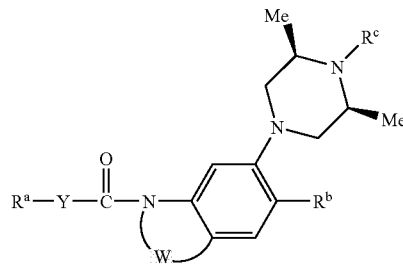

| Example | Rᵃ—Y— | W | Rᵇ | Rᶜ | MH⁺ |
|---|---|---|---|---|---|
| E3 | MeSO₂NH-(2-Me-pyridin-6-yl)-(4-phenyl)- | CH₂CH₂ | OMe | H | 550 |
| E4 | MeCON(Me)-(2-Me-pyridin-6-yl)-(4-phenyl)- | CH₂CH₂ | OMe | H | 528 |
| E5 | MeSO₂N(Me)-(2-Me-pyridin-6-yl)-(4-phenyl)- | CH₂CH₂ | OMe | H | 564 |
| E6 | MeSO₂N(Me)-(2-Me-pyridin-6-yl)-(4-phenyl)- | CH₂CH₂ | F | H | 552 |
| E7 | MeCONH-(2-Me-phenyl)-(4-phenyl)- | CH₂CH₂ | OMe | H | 513 |
| E8 | MeSO₂NH-(2-Me-phenyl)-(4-phenyl)- | CH₂CH₂ | OMe | H | 549 |
| E9 | MeCONH-(2-Me-phenyl)-(4-phenyl)- | CH₂CH₂ | F | H | 501 |
| E10 | MeCONH-(2-Me-phenyl)-(4-phenyl)- | CH₂CH₂ | F | H | 537 |
| E11 | MeCONCH₂H-(2-Me-phenyl)-(4-phenyl)- | CH₂CH₂ | OMe | H | 527 |

-continued
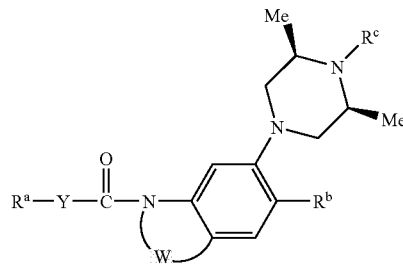
| Example | Rª—Y— | W | R^b | R^c | MH⁺ |
|---|---|---|---|---|---|
| E12 | MeCONCH₂(H)-[2-Me-biphenyl]- | CH₂CH₂ | Me | H | 511 |
| E13 | MeCONCH₂(H)-[2-Me-biphenyl]- | CH₂CH₂ | F | H | 515 |
| E14 | MeCONCH₂(H)-[2-Me-biphenyl]- | CH₂CH₂ | Cl | H | 531/533 |
| E15 | MeSO₂N(H)-[2-Me-biphenyl]- | CH=CH | F | H | 535 |
| E16 | MeSO₂N(Me)-[2-Me-pyridyl-phenyl]- | CH=CH | F | H | 550 |
| E17 | MeCONCH₂(H)-[2-Me-biphenyl]- | CH=CH | F | H | 513 |
| E18 | MeCONCH₂(H)-[2-Me-biphenyl]- | CH=CH | Cl | H | 529/531 |
| E19 | MeCONCH₂(H)-[2-Me-biphenyl]- | CH=CH | Me | H | 509 |
| E20 | MeCON(Me)-[2-Me-pyridyl-phenyl]- | CH=CH | F | H | 514 |

-continued
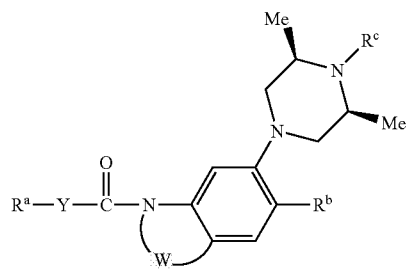
| Example | Rᵃ—Y— | W | Rᵇ | Rᶜ | MH⁺ |
|---|---|---|---|---|---|
| E21 | MeSO₂NH—(6-position)-2-Me-pyridin-3-yl-(4-phenylene)— | CH₂CH₂ | F | H | 538 |
| E22 | MeCONH—(6-position)-2-Me-pyridin-3-yl-(4-phenylene)— | CH₂CH₂ | F | H | 502 |
| E23 | MeCON(Me)—(6-position)-2-Me-pyridin-3-yl-(4-phenylene)— | CH₂CH₂ | F | H | 516 |
| E24 | MeSO₂N(Me)—(2-Me-biphenyl-4'-yl)— | CH₂CH₂ | F | H | 551 |
| E25 | MeCON(Me)—(2-Me-biphenyl-4'-yl)— | CH₂CH₂ | F | H | 515 |
| E26 | MeCONH—(2-Me-biphenyl-4'-yl)— | CH₂CH₂ | OMe | Me | 527 |
| E27 | MeCONHCH₂—(2-Me-biphenyl-4'-yl)— | CH₂CH₂ | OMe | Me | 541 |

The invention claimed is:
1. A compound of formula (I) or a pharmaceutically acceptable salt thereof:

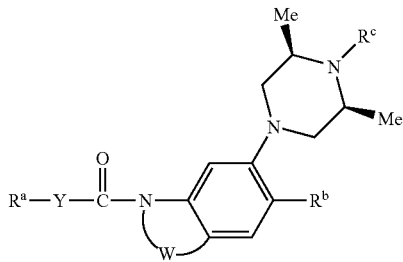

in which $R^a$ is a group of formula (i):

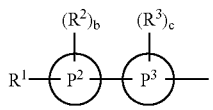

wherein
P² is phenyl, naphthyl, or pyridyl;
P³ is phenyl, naphthyl or or pyridyl;
R¹ is NR⁴COR⁵, NR⁴SO₂R⁵, CH₂NR⁴SO₂R⁵, CH²NR⁴COR⁵ or CH₂NR⁴CO₂R⁵ where R⁴ and R⁵ are independently hydrogen or C₁₋₆alkyl;
R² and R³ are independently halogen, C₁₋₆alkyl, C₃₋₆cycloalkyl, C₁₋₆alkoxy, COC₁₋₆alkyl, CF₃, cyano or NR⁶R⁷ where R⁶ and R⁷ independently hydrogen or C₁₋₆alkyl;
b and c are independently 0, 1, 2 or 3;
Y is a single bond, CH₂ or NH;
W is —(CR⁹R¹⁰)- where t is 2, 3 or 4 and R⁹ and R¹⁰ are independently hydrogen or C₁₋₆alkyl or W is a group CH=CH;
$R^b$ is hydrogen, halogen, C₁₋₆alkyl, CF₃, COC₁₋₆alkyl, cyano or C₁₋₆alkoxy;
$R^c$ is hydrogen or C₁₋₆alkyl.

2. A compound according to claim 1 in which, within the group $R^a$, P² and P³ are independently phenyl or pyridyl.
3. A compound according to claim 2 in which Y is a single bond.
4. A compound according to claim 1 in which $R^b$ is hydrogen, halogen, C₁₋₆alkoxy or C₁₋₆alkyl.
5. A compound according to claim 1 in which W is —CH₂—CH₂— or —CH=CH—.
6. A compound according to claim 1 in which $R^c$ is hydrogen or methyl.
7. A pharmaceutical composition which comprises a compound according to claim 1 or a pharmaceutically acceptable salt thereof and a pharmaceutically acceptable carrier or excipient.
8. A method of treating depression which comprises administering a safe and therapeutically effective amount of compound of formula (I) according to claim 1 or a pharmaceutically acceptable salt to a patient in need thereof.
9. A compound according to claim 1 which is:
N-[5-(4-{6-[(3R,5S)-3,5-dimethyl-1-piperazinyl]-5-(methoxy)-2,3-dihydro-1H-indol-1-yl]carbonyl}phenyl)-6-methyl-2-pyridinyl]acetamide;
N-[4'-({6-[(3R,5S)-3,5-dimethyl-1-piperazinyl]-5-fluoro-1H-indol-1-yl}carbonyl-2-methyl-4-biphenylyl]acetamide;
N-[5-(4-{[6-[(3R,5S)-3,5-dimethyl-1-piperazinyl]-5-(methoxy)-2,3-dihydro-1H-indol-1-yl]carbonyl}phenyl)-6-methyl-2-pyridinyl]methanesulfonamide;
N-[5-(4-{[6-[(3R,5S)-3,5-dimethyl-1-piperazinyl]-5-(methoxy)-2,3-dihydro-1H-indol-1-yl]carbonyl}phenyl)-6-methyl-2-pyridinyl]-N-methylacetamide;
N-[5-(4-{[6-[(3R,5S)-3,5-dimethyl-1-piperazinyl]-5-(methoxy)-2,3-dihydro-1H-indol-1-yl]carbonyl}phenyl)-6-methyl-2-pyridinyl]-N-methylmethanesulfonamide;
N-{5-[4-({6-[(3R,5S)-3,5-dimethyl-1-piperazinyl]-5-fluoro-2,3-dihydro-1H-indol-1-yl}carbonyl)phenyl]-6-methyl-2-pyridinyl}-N-methylmethanesulfonamide;
N-(4'-{[6-[(3R,5S)-3,5-dimethyl-1-piperazinyl]-5-(methoxy)-2,3-dihydro-1H-indol-1-yl]carbonyl}-2-methyl-4-biphenylyl)acetamide;
N-(4'-{[6-[(3R,5S)-3,5-dimethyl-1-piperazinyl]-5-(methoxy)-2,3-dihydro-1H-indol-1-yl]carbonyl}-2-methyl-4-biphenylyl)methanesulfonamide;
N-[4'-({6-[(3R,5S)-3,5-dimethyl-1-piperazinyl]-5-fluoro-2,3-dihydro-1H-indol-1-yl}carbonyl)-2-methyl-4-biphenylyl]acetamide;
N-[4'-({6-[(3R,5S)-3,5-dimethyl-1-piperazinyl]-5-fluoro-2,3-dihydro-1H-indol-1-yl}carbonyl)-2-methyl-4-biphenylyl]methanesulfonamide;
N-[(4'-{[6-[(3R,5S)-3,5-dimethyl-1-piperazinyl]-5-(methoxy)-2,3-dihydro-1H-indol-1-yl]carbonyl}-2-methyl-4-biphenylyl)methyl]acetamide;
N-{[4'-({6-[(3R,5S)-3,5-dimethyl-1-piperazinyl]-5-methyl-2,3-dihydro-1H-indol-1-yl}carbonyl)-2-methyl-4-biphenylyl]methyl}acetamide;
N-{[4'-({6-[(3R,5S)-3,5-dimethyl-1-piperazinyl]-5-fluoro-2,3-dihydro-1H-indol-1-yl}carbonyl)-2-methyl-4-biphenylyl]methyl}acetamide;
N-{[4'-({5-chloro-6-[(3R,5S)-3,5-dimethyl-1-piperazinyl]-2,3-dihydro-1H-indol-1-yl}carbonyl)-2-methyl-4-biphenylyl]methyl}acetamide;
N-[4'-({6-[(3R,5S)-3,5-dimethyl-1-piperazinyl]-5-fluoro-1H-indol-1-yl}carbonyl)-2-methyl-4-biphenylyl]methanesulfonamide;
N-{5-[4-({6-[(3R,5S)-3,5-dimethyl-1-piperazinyl]-5-fluoro-1H-indol-1-yl}carbonyl)phenyl]-6-methyl-2-pyridinyl}-N-methylmethanesulfonamide;
N-{[4'-({6-[(3R,5S)-3,5-dimethyl-1-piperazinyl]-5-fluoro-1H-indol-1-yl}carbonyl)-2-methyl-4-biphenylyl]methyl}acetamide;
N-{[4'-({5-chloro-6-[(3R,5S)-3,5-dimethyl-1-piperazinyl]-1H-indol-1-yl}carbonyl)-2-methyl-4-biphenylyl]methyl}acetamide;
N-{[4'-({6-[(3R,5S)-3,5-dimethyl-1-piperazinyl]-5-methyl-1H-indol-1-yl}carbonyl)-2-methyl-4-biphenylyl]methyl}acetamide;
N-{5-[4-({6-[(3R,5S)-3,5-dimethyl-1-piperazinyl]-5-fluoro-1H-indol-1-yl}carbonyl)phenyl]-6-methyl-2-pyridinyl}-N-methylacetamide;
N-{5-[4-({6-[(3R,5S)-3,5-dimethyl-1-piperazinyl]-5-fluoro-2,3-dihydro-1H-indol-1-yl}carbonyl)phenyl]-6-methyl-2-pyridinyl}methanesulfonamide;
N-{5-[4-({6-[(3R,5S)-3,5-dimethyl-1-piperazinyl]-5-fluoro-2,3-dihydro-1H-indol-1-yl}carbonyl)phenyl]-6-methyl-2-pyridinyl}acetamide;

N-{5-[4-({6-[(3R,5S)-3,5-dimethyl-1-piperazinyl]-5-fluoro-2,3-dihydro-1H-indol-1-yl}carbonyl)phenyl]-6-methyl-2-pyridinyl}-N-methylacetamide;

N-[4'-({6-[(3R,5S)-3,5-dimethyl-1-piperazinyl]-5-fluoro-2,3-dihydro-1H-indol-1-yl}carbonyl)-2-methyl-4-biphenylyl]-N-methylmethanesulfonamide;

N-[4'-({6-[(3R,5S)-3,5-dimethyl-1-piperazinyl]-5-fluoro-2,3-dihydro-1H-indol-1-yl}carbonyl)-2-methyl-4-biphenylyl]-N-methylacetamide;

N-[2-methyl-4'-({5-(methyloxy)-6-[(3R,5S)-3,4,5-trimethyl-1-piperazinyl]-2,3-dihydro-1H-indol-1-yl}carbonyl)-4-biphenylyl]acetamide;

N-{[2-methyl-4'-({5-(methyloxy)-6-[(3R,5S)-3,4,5-trimethyl-1-piperazinyl]-2,3-dihydro-1H-indol-1-yl}carbonyl)-4-biphenylyl]methyl}acetamide; or a pharmaceutically acceptable salt thereof.

\* \* \* \* \*